United States Patent
Chen et al.

(10) Patent No.: US 12,194,199 B2
(45) Date of Patent: *Jan. 14, 2025

(54) INTRAVASCULAR DEVICES

(71) Applicants: STRYKER CORPORATION, Kalamazoo, MI (US); STRYKER EUROPEAN OPERATIONS LIMITED, Carrigtwohill (IE)

(72) Inventors: Hancun Chen, San Ramon, CA (US); Andrew S. Lee, San Jose, CA (US)

(73) Assignees: Stryker Corporation, Kalamazoo, MI (US); Stryker European Operations Limited, Carrigtwohill (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/498,803

(22) Filed: Oct. 31, 2023

(65) Prior Publication Data

US 2024/0058510 A1  Feb. 22, 2024

Related U.S. Application Data

(63) Continuation of application No. 18/315,502, filed on May 11, 2023, which is a continuation of application
(Continued)

(51) Int. Cl.
*A61L 31/14* (2006.01)
*A61L 31/02* (2006.01)
(Continued)

(52) U.S. Cl.
CPC ............. *A61L 31/022* (2013.01); *A61L 31/14* (2013.01); *A61B 17/1214* (2013.01);
(Continued)

(58) Field of Classification Search
CPC .................................... A61L 31/022
See application file for complete search history.

(56) References Cited

U.S. PATENT DOCUMENTS 6,051,021 A    4/2000  Frid
6,322,576 B1 * 11/2001 Wallace ........... A61B 17/12113
                                                    606/198
(Continued)

FOREIGN PATENT DOCUMENTS

CN    109385591       2/2019
CN    109385591 A  *  2/2019  ............. B21C 37/04
(Continued)

OTHER PUBLICATIONS

Lou et al. CN109385591 translation. 2018 (Year: 2018).*
(Continued)

*Primary Examiner* — Cachet I Proctor
(74) *Attorney, Agent, or Firm* — Vista IP Law Group, LLP

(57) ABSTRACT

An implantable medical device includes an elongate member having a cross-sectional dimension that is less than 0.00085 inch, wherein the elongate member is made from a material comprising a platinum-tungsten alloy having a percentage of tungsten that is at least 10% by weight or alternatively the implantable medical device includes an elongate member made from a material comprising an alloy containing rhenium.

19 Claims, 5 Drawing Sheets

FIG. 1B

Related U.S. Application Data

No. 18/176,435, filed on Feb. 28, 2023, which is a continuation of application No. 16/872,124, filed on May 11, 2020, now Pat. No. 11,612,678, which is a continuation-in-part of application No. 16/567,845, filed on Sep. 11, 2019, now Pat. No. 11,484,629.

(51) Int. Cl.
| | |
|---|---|
| *C22C 5/04* | (2006.01) |
| *A61B 17/12* | (2006.01) |
| *A61F 2/01* | (2006.01) |
| *A61F 2/06* | (2013.01) |
| *A61F 2/90* | (2013.01) |
| *A61F 2/95* | (2013.01) |
| *C22C 27/04* | (2006.01) |

(52) U.S. Cl.
CPC ... *A61F 2002/016* (2013.01); *A61F 2002/068* (2013.01); *A61F 2/90* (2013.01); *A61F 2/95* (2013.01); *C22C 5/04* (2013.01); *C22C 27/04* (2013.01)

(56) References Cited

U.S. PATENT DOCUMENTS

| | | | |
|---|---|---|---|
| 6,458,119 B1 * | 10/2002 | Berenstein | A61B 17/1214 606/1 |
| 7,250,058 B1 * | 7/2007 | Pacetti | A61L 31/18 606/198 |
| 7,842,054 B2 | 11/2010 | Greene, Jr. et al. | |
| 9,060,777 B1 * | 6/2015 | Wallace | A61F 2/07 |
| 9,198,670 B2 | 12/2015 | Hewitt et al. | |
| 9,597,155 B2 | 3/2017 | Schewe et al. | |
| 11,484,629 B2 | 11/2022 | Chen et al. | |
| 11,795,524 B2 | 10/2023 | Horinouchi et al. | |
| 2003/0077200 A1 | 4/2003 | Craig et al. | |
| 2004/0193205 A1 | 9/2004 | Burgermeister | |
| 2004/0220608 A1 | 11/2004 | D'aquanni et al. | |
| 2005/0065545 A1 | 3/2005 | Wallace | |
| 2005/0070990 A1 | 3/2005 | Stinson | |
| 2006/0116711 A1 * | 6/2006 | Elliott | A61B 17/12022 606/200 |
| 2006/0153729 A1 | 7/2006 | Stinson et al. | |
| 2006/0198750 A1 | 9/2006 | Furst et al. | |
| 2007/0067009 A1 | 3/2007 | Gandhi et al. | |
| 2007/0162108 A1 | 7/2007 | Carlson et al. | |
| 2007/0280850 A1 | 12/2007 | Carlson | |
| 2008/0185075 A1 * | 8/2008 | Ishida | C22C 19/07 148/408 |
| 2008/0195194 A1 | 8/2008 | Pacetti et al. | |
| 2009/0192585 A1 | 7/2009 | Bloom et al. | |
| 2015/0283363 A1 | 10/2015 | Hewitt et al. | |
| 2016/0066918 A1 | 3/2016 | Chen | |
| 2017/0226362 A1 | 8/2017 | Fratello et al. | |
| 2018/0263629 A1 * | 9/2018 | Murphy | A61B 17/12154 |
| 2018/0325706 A1 | 11/2018 | Hebert et al. | |
| 2019/0374228 A1 * | 12/2019 | Wallace | A61B 17/1214 |
| 2020/0149137 A1 | 5/2020 | Roth | |
| 2021/0069386 A1 | 3/2021 | Chen et al. | |
| 2021/0069387 A1 | 3/2021 | Chen et al. | |

FOREIGN PATENT DOCUMENTS

| | | |
|---|---|---|
| JP | 2005-233967 | 9/2005 |
| JP | 2006-129935 | 5/2006 |
| JP | 2016-130351 | 7/2016 |
| JP | 2020-111795 | 7/2020 |
| WO | WO 2004/022122 | 3/2004 |
| WO | WO 2019/014206 | 1/2019 |
| WO | WO-2019014206 A1 * | 1/2019 ............ A61B 17/00 |

OTHER PUBLICATIONS

Final Office Action for U.S. Appl. No. 18/315,502 dated Apr. 11, 2024.
Non-Final Office Action for U.S. Appl. No. 18/176,435 dated Jul. 5, 2024.
Non-Final Office Action for U.S. Appl. No. 18/187,435 dated Feb. 20, 2024.
Foreign Rejection Decision for CN Patent Appln. No. 202080062884.7 dated May 17, 2024 (With translated English comments from examiner).
Non-Final Office Action for U.S. Appl. No. 18/315,502 dated Dec. 21, 2023.
Foreign OA for CN Patent Appln. No. 202080062884.7 dated Dec. 5, 2023 (with English translation provided by foreign agent).
Amendment Response to NFOA for U.S. Appl. No. 18/176,435 dated Oct. 24, 2023.
Foreign Comm Response for EP Patent Appln. No. 23153653.3 dated Jan. 30, 2024.
Foreign OA for CN Patent Appln. No. 202080062884.7 dated Mar. 12, 2024 (with English translation of Examiner's Comments).
PCT Invitation to Pay Additional Fees for International Appln. No. PCT/US2020/050175, Applicant Magic Leap, Inc., dated Dec. 10, 2020 (11 pages).
PCT International Search Report and Written Opinion for International Appln. No. PCT/US2020/050175, Applicant Stryker Corporation, dated Mar. 19, 2021 (17 pages).
Non-Final Office Action for U.S. Appl. No. 16/567,845 dated Mar. 31, 2022.
Foreign OA for CN Patent Appln. No. 202080062884.7 dated Jun. 1, 2023 (with English translation provided by foreign examiner).
Non-Final Office Action for U.S. Appl. No. 18/176,435 dated Sep. 28, 2023.
Non-Final Office Action for U.S. Appl. No. 16/872,124 dated Apr. 14, 2022.
Final Office Action for U.S. Appl. No. 16/872,124 dated Nov. 1, 2022.
Notice of Allowance for U.S. Appl. No. 16/872,124 dated Dec. 8, 2022.
Notice of Allowance for U.S. Appl. No. 16/567,845 dated Jun. 29, 2022.
Non-Final Office Action for U.S. Appl. No. 17/940,965 dated Mar. 16, 2023.
Notice of Allowance for U.S. Appl. No. 17/940,965 dated Jun. 23, 2023.
Umeda M., et al., "Methanol electrooxidation at Pt—Ru—W sputter deposited on Au substrate," Journal of Power Sources, Elsevier, Amsterdam, NL, vol. 136, No. 1,Sep. 10, 2004, pp. 10-15, XP004544508, ISSN: 0378-7753, DOI: 10.1016/J.JPOWSOUR. 2004.05.013 Section 2(c) Pt-W, figure 1.
Extended European Search Report issued in corresponding European Patent Application No. 22184685, dated Dec. 14, 2022.
Foreign Exam Report for IN Patent Appln. No. 202247011359 dated Sep. 4, 2024.

* cited by examiner

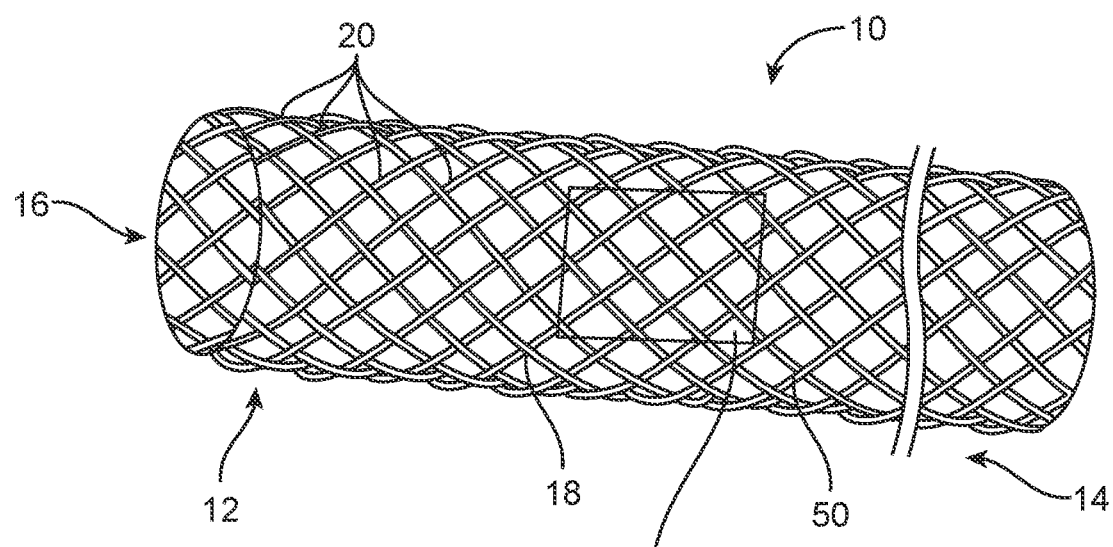
FIG. 1A
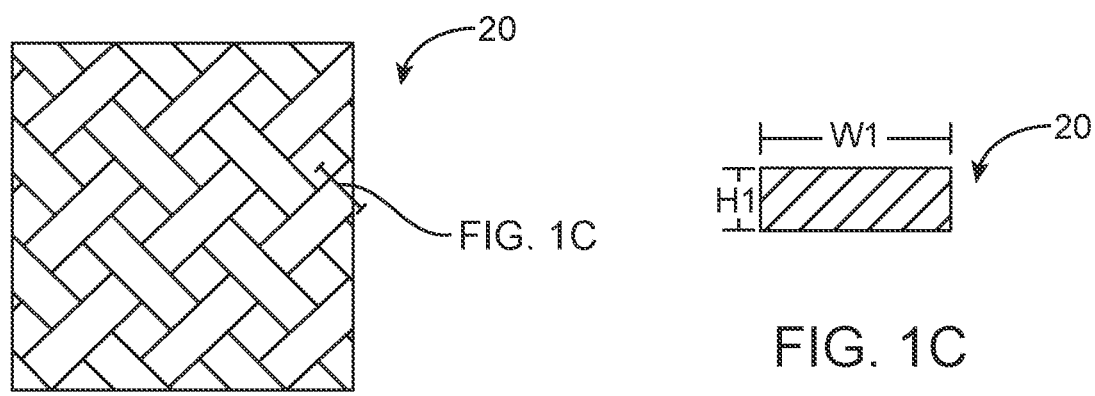
FIG. 1B
FIG. 1C

INTRAVASCULAR DEVICES

RELATED APPLICATION DATA

This application is a continuation of U.S. patent application Ser. No. 18/315,502, filed on May 11, 2023, which is a continuation of U.S. patent application Ser. No. 18/176,435, filed on Feb. 28, 2023, which is a continuation of U.S. patent application Ser. No. 16/872,124, filed on May 11, 2020, now issued as U.S. Pat. No. 11,612,678, which is a continuation-in-part of U.S. patent application Ser. No. 16/567,845, filed on Sep. 11, 2019, now U.S. Pat. No. 11,484,629, the contents of all of which are hereby incorporated herein by reference in their entirety into the present application.

FIELD

The present disclosure relates generally to medical devices. More particularly, the present disclosure relates to medical devices, such as intravascular implants.

BACKGROUND

The use of intravascular medical devices has become an effective method for treating many types of vascular disease. Intravascular medical devices such as stents, filters, thromboembolic capture devices, flow diverters, vaso-occlusive devices, collectively referred to herein as "medical devices" are often composed of a variety of biocompatible materials, including polymers (e.g., non-biodegradable and biodegradable plastics) and/or metals. Some of these medical devices are formed by one or more elongate members (e.g., wires, drawn-filled tubes, threads, filaments and the like) that are woven into a braid or mesh pattern. Such braided devices may be utilized for treating various types of vascular defects, such as aneurysms, and may be provided in a wide variety of respective delivery and deployed sizes and shapes; particularly, secondary shapes when the device is deployed in a targeted vasculature site. Some exemplary secondary shapes of braided devices include spherical, ovoid, flat ribbon, helical braided ribbon, or combinations thereof, suitable for the treatment of vascular defects. In general, a suitable intravascular implantable device is inserted into the vascular system of the patient and navigated through the vasculature to a targeted implantation site using known delivery systems and methods.

Medical devices can be made from shape memory or superelastic materials, such as shape memory metals (e.g., shape memory Nitinol) and polymers (e.g., polyurethane). Such shape memory embolic devices can be induced (e.g., by temperature, electrical or magnetic field or light) to take on a shape (e.g., a radially expanded shape) after delivery to a treatment site. Superelastic materials, such as superelastic Nitinol, take on a shape after delivery without the need for an inductive stimulus. Drug delivery medical devices can carry, and/or the surface of the device, can be coated with a bioactive or therapeutic agent (e.g., thrombosis inducing agent).

Various physical attributes of the medical devices can contribute directly to the success rate of the device. These physical attributes include radiopacity, hoop strength, radial force, column strength, flexibility and dimensions of the material used to form the device and the like. Cobalt-chromium (Co—Cr) and stainless steel are commonly used to form stents. These materials are commonly used since such materials having a known history of safety, effectiveness and biocompatibility. These materials however have limited physical performance characteristics as to size, strength, weight, bendability, biostability and radiopacity.

Other commonly used materials include platinum, platinum and tungsten metal alloy, and Elgiloy. Known medical devices composed of platinum-tungsten alloy (Pt—W) are illustrated and described (by way of example) in U.S. Pat. Nos. 6,322,576, 6,458,119, 7,842,054, 9,198,670 and 9,597,155, and U.S. Publication No. 20070162108. However, these disclosures are either silent with respect to the specific percentage of platinum and tungsten in the metal alloy or they expressly disclose a preferred or desirable combination of the alloy having platinum (92%) and tungsten (8%) (i.e., Pt-8% wtW).

Due to higher modulus and mechanical strength, some more recent implantable devices including blood flow diversion stents are being made out of cobalt-chromium (Co—Cr) alloys designed to have suitable radial force. However, the Co—Cr devices have undesirable properties, such as substantially higher magnetic susceptibility of Magnetic Resonance Imaging (MRI) resulting in MR image artifact and poor radiopacity. For the known platinum-tungsten (Pt—W) alloys, up to 8% tungsten (W) has been alloyed to the platinum (Pt) to enhance mechanical strength, handling, and manufacturability. Alloying tungsten (W) greater than 8% is not generally considered because additional tungsten (W) in the platinum (Pt) matrix generally increases its brittleness, compromising the performance of the Pt—W alloy. Although commonly used Pt-8% wtW alloy has relatively low magnetic susceptibility of MRI and higher radiopacity than Co—Cr, the Pt-8% wtW alloy has been found to be not suitable for such flow diversion stents due to the low modulus of the alloy, which results in an undesirably low radial expansion force. In particular, the 8% tungsten (W) was added to the platinum (Pt) alloy to enhance mechanical strength, handling and manufacturability. However, adding more than 8% tungsten (W) has not been explored due to expected increased brittleness of the Pt—W alloy.

SUMMARY

Embodiments described herein are directed to implantable medical devices, such as embolic devices and blood flow filters, that are at least partially made out of (i.e., composed of) a platinum-tungsten alloy in which a percentage of tungsten in the alloy is equal to or greater than about 10% by weight, such as in a range of between about 10% to about 25% by weight, or more preferably between about 10% to about 20% by weight.

In various embodiments, the implantable devices are made out of one or more elongate members composed of the platinum-tungsten alloy, such as in the form of a cut tube, a coiled wire, or a plurality of wires woven in a braided configuration. Without limitation, the elongate members may include composite wires having at least one layer made out of the platinum-tungsten alloy. In other embodiments, the elongate members may include composite wires having at least one layer made out of an alloy containing rhenium.

Although it has been traditionally believed in the art of making implantable medical devices that a platinum-tungsten alloy having a percentage of tungsten over 8% is not manufacturable, through experiment, the present inventors discovered that a platinum-tungsten alloy having a percentage of tungsten that is at least 10% by weight could not only be manufactured but would unexpectantly have several advantageous properties. By way of example, and without limitation, such unexpected advantageous properties include having a substantially greater ultimate tensile strength, a substantially greater Young's modulus, and a substantially reduced magnetic susceptibility, than those in identically dimensioned alternative materials composed of a platinum-tungsten alloy having a percentage of tungsten that is about 8% by weight.

Utilizing the materials disclosed herein, one or more elongate members of an implantable medical device may be made to have a very small cross-sectional dimension, such as a cross-sectional dimension that is less than 0.00085 inch, and preferably between 0.0001 inch to 0.0008 inch, and more preferably between 0.0003 inch to 0.00075 inch.

In accordance with some embodiments, an implantable medical device includes: an elongate member having a cross-sectional dimension that is less than 0.00085 inch; wherein the elongate member is made from a material comprising a platinum-tungsten alloy having a percentage of tungsten that is at least 10% by weight.

Optionally, the implantable medical device has a longitudinal axis and a length measured in a direction of the longitudinal axis that is at least 1.2 inch; wherein the implantable medical device is insertable lengthwise into a tube having a lumen, at least a part of the lumen having a diameter not greater than 0.02 inch; and wherein the implantable medical device has a column strength sufficient to allow the implantable medical device to be pushed through the lumen without undergoing buckling, kinking, or plastic deformation.

Optionally, the implantable medical device has a first radius of curvature, R1, when in a relaxed configuration before insertion into a catheter, and a second radius of curvature, R2, after the implantable medical device has been inserted into the catheter and delivered out of the catheter, and wherein R2 is less than five times R1.

Optionally, the elongate member has a greater ultimate tensile strength, a greater Young's modulus, and a lesser magnetic susceptibility, respectively, than those of an identically dimensioned alternative elongate member composed of an alternative platinum-tungsten alloy having a percentage of tungsten that is 8% by weight.

Optionally, the cross-sectional dimension of the elongate member is anywhere from 0.0001 inch to 0.0008 inch.

Optionally, the cross-sectional dimension of the elongate member is anywhere from 0.0003 inch to 0.00075 inch.

Optionally, the material has a Young' modulus of 30 Msi or higher.

Optionally, the material has an ultimate tensile strength (UTS) that is 350 ksi or higher.

Optionally, the elongate member forms a part of a braid.

Optionally, the implantable medical device further includes a first coil segment at a first end of the braid.

Optionally, the implantable medical device further includes a second coil segment at a second end of the braid.

Optionally, the first coil segment is made from a coil wire having a cross-sectional dimension that is anywhere from 0.0001 inch to 0.002 inch, and wherein the first coil segment has a primary wind diameter that is anywhere from 0.003 inch to 0.030 inch.

Optionally, the braid has a wire count that is anywhere from 8 to 96, from 16 to 32, from 24 to 144, or from 24 to 72.

Optionally, the braid comprises a flat braid.

Optionally, the material also comprises Ta, Ir, Re, Rh, Ru, Mo, Zr, Hf, Au, or any combination of the foregoing.

Optionally, the elongate member is a drawn-filled tube.

A kit includes the implantable medical device and a catheter.

Optionally, a maximum lumen width of at least a part of the catheter is less than 0.014 inch.

In accordance with other embodiments, an implantable medical device includes: an elongate member made from a material comprising an alloy containing rhenium.

Optionally, the elongate member has a cross-sectional dimension that is less than 0.00085 inch.

Optionally, the elongate member has a cross-sectional dimension that is anywhere from 0.0001 inch to 0.0008 inch.

Optionally, the elongate member has a cross-sectional dimension that is anywhere from 0.0003 inch to 0.00075 inch.

Optionally, the alloy comprises a molybdenum-rhenium alloy.

Optionally, the alloy comprises a tungsten-rhenium alloy.

Optionally, the implantable medical device has a longitudinal axis and a length measured in a direction of the longitudinal axis that is at least 1.2 inch; wherein the implantable medical device is insertable lengthwise into a tube having a lumen, at least a part of the lumen having a diameter not greater than 0.02 inch; and wherein the implantable medical device has a column strength sufficient to allow the implantable medical device to be pushed through the lumen without undergoing buckling, kinking, or plastic deformation.

Optionally, the implantable medical device has a first radius of curvature, R1, when in a relaxed configuration before insertion into a catheter, and a second radius of curvature, R2, after the implantable medical device has been inserted into the catheter and delivered out of the catheter, and wherein R2 is less than five times R1.

Optionally, the elongate member has a greater ultimate tensile strength, a greater Young's modulus, and a lesser magnetic susceptibility, respectively, than those of an identically dimensioned alternative elongate member composed of an alternative platinum-tungsten alloy having a percentage of tungsten that is 8% by weight.

Optionally, the material has a Young' modulus of 30 Msi or higher.

Optionally, the material has an ultimate tensile strength (UTS) that is 350 ksi or higher.

Optionally, the elongate member forms a part of a braid.

Optionally, the implantable medical device further includes a first coil segment at a first end of the braid.

Optionally, the implantable medical device further includes a second coil segment at a second end of the braid.

Optionally, the first coil segment is made from a coil wire having a cross-sectional dimension that is anywhere from 0.0001 inch to 0.002 inch, and wherein the first coil segment has a primary wind diameter that is anywhere from 0.003 inch to 0.030 inch.

Optionally, the braid has a wire count that is anywhere from 8 to 96, from 16 to 32, from 24 to 144, or from 24 to 72.

Optionally, the braid comprises a flat braid.

Optionally, the material also comprises Ta, Ir, Rh, Ru, Mo, Zr, Hf, Au, or any combination of the foregoing.

Optionally, the elongate member is a drawn-filled tube.

A kit includes the implantable medical device and a catheter.

Optionally, a maximum lumen width of at least a part of the catheter is less than 0.014 inch.

In accordance with other embodiments, an implantable medical device includes: an elongate member having a cross-sectional dimension that is less than 0.00085 inch; wherein the implantable medical device has a longitudinal axis and a length measured in a direction of the longitudinal axis that is at least 1.2 inch; wherein the implantable medical device is insertable lengthwise into a tube having a lumen, at least a part of the lumen having a diameter not greater than 0.02 inch; and wherein the implantable medical device has a column strength sufficient to allow the implantable medical device to be pushed through the lumen without undergoing buckling, kinking, or plastic deformation.

Other and further aspects and features of the embodiments will become apparent from the ensuing detailed description in view of the accompanying figures.

BRIEF DESCRIPTION OF THE DRAWINGS

FIGS. 1A-1C are perspective, detailed and cross-sectional views of a braided stent/flow diverter constructed according to some embodiments;

DETAILED DESCRIPTION OF THE ILLUSTRATED EMBODIMENTS

Figure 2A:
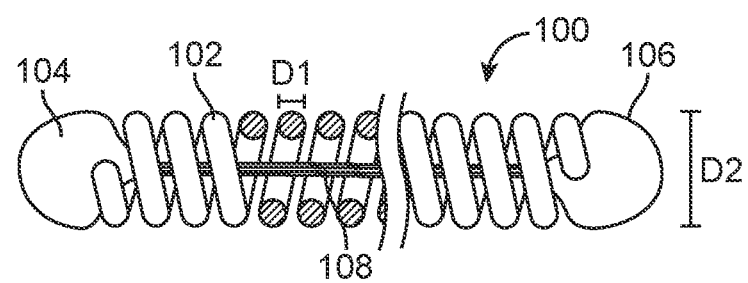
FIGS. 2A-2B are cross-sectional and perspective and view of an embolic coil constructed according to some embodiments.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. The figures are not necessarily drawn to scale, the relative scale of select elements may have been exaggerated for clarity, and elements of similar structures or functions are represented by like reference numerals throughout the figures. It should also be understood that the figures are only intended to facilitate the description of the embodiments, and are not intended as an exhaustive description of the disclosed inventions, or as a limitation on the scope thereof, which is defined only by the appended claims and their equivalents.

In addition, the respective illustrated embodiments of the disclosed inventions need not have all of the depicted features, and a feature, aspect or advantage described in conjunction with a particular embodiment is not necessarily limited to that embodiment, but can be practiced in other embodiments, even if not so illustrated.

Metal Alloy

In various embodiments described herein, a metal alloy comprising platinum and tungsten (Pt—W) having a percentage (i.e., hereafter mass or weight percentage) of tungsten (W) that is equal or larger than 10% of the alloy, is used in the manufacturing of medical devices. In some embodiments, the percentage of tungsten (W) ranges from 10% to 25%, and more preferably from 10% to 20%, of the alloy. In those embodiments the remaining percentage of the alloy is composed mostly of platinum (Pt), such as for example, where the percentage of platinum (Pt) is equal or less than 90% of the alloy when the percentage of tungsten (W) that is equal or larger than 10%, or where the percentage of platinum (Pt) is equal or less than 80% of the alloy when the percentage of tungsten (W) that is equal or larger than 20%.

In one or more embodiments described herein, the percentage of tungsten (W) is equal or larger than 10% of the platinum-tungsten (Pt—W) alloy used to form the medical devices. Having the percentage of tungsten (W) as equal or larger than 10% of the platinum-tungsten (Pt—W) alloy forming the medical devices provides for improved properties compared to known medical devices having 8% or less of tungsten (W) in the platinum-tungsten (Pt—W) alloy.

As noted above, although conventional wisdom has been that it is not advisable to increase the percentage of tungsten in a platinum-tungsten alloy used for constructing implantable medical devices, the present inventors, when considering and studying the Pt—W phase diagram, believed that Pt-high W content alloys may nonetheless be of some value. From theoretical analysis, the inventors expected there might be some improvements in mechanical strength of the resulting alloy. However, experimentation using Pt-16% W alloy demonstrated exceptionally good and unexpected results with respect to improved mechanical properties, increase in radiopacity (which is critical for blood flow diverter devices) and, most surprisingly, a substantial reduction in magnetic susceptibility (little or no change had been expected).

These unexpected properties of the disclosed platinum-tungsten (Pt—W) alloy comprises one or more of the following exemplary properties, such as: column strength, radial strength, hoop strength, tensile strength, tensile elongation, stress-strain properties, radial force, radiopacity, flexibility, bendability, heat sensitivity, biocompatibility, and the like. Particularly, a medical device composed of a percentage of tungsten (W) that is equal or larger than 10% of the platinum-tungsten (Pt—W) alloy may increase: radiopacity, radial strength, hardness, yield strength and/or ultimate tensile strength of the device; and/or may further improve stress-strain properties of the device, crimping and/or expansion properties, bendability and/or flexibility, overall strength and/or durability of the device, longitudinal lengthening properties, recoil properties, friction coefficient, heat sensitivity properties, biostability and/or biocompatibility properties, and/or enable manufacturing of smaller, thinner and/or lighter weight medical devices. For example, a medical device composed of a percentage of tungsten (W) that is equal or larger than 10% of the platinum-tungsten (Pt—W) alloy, is configured to have a Young's modulus of equal or larger than 30 Ksi. Additionally, or alternatively, medical devices composed of a percentage of tungsten (W) that is equal or larger than 10% of the platinum-tungsten (Pt—W) alloy are configured to have a magnetic susceptibility in the range of 10 ppm to 300 ppm resulting in reduced artifact during MR imaging.

For example, current flow diversion stents composed of cobalt-chromium (Co—Cr) alloys have substantially higher magnetic susceptibility of MRI (i.e., MR artifact) and poor radiopacity. Thus, making MR follow up imaging not suitable for implanted flow diversion stents made of Co—Cr. In some instances, to improve radiopacity of flow diversion stents made of Co—Cr, Pt-8% W alloy wires are blended with Co—Cr wires. However, flow diversion stents composed of a percentage of tungsten (W) that is equal or larger than 10% of the platinum-tungsten (Pt—W) alloy allows for a suitable superior radiopacity and radial force due to the high modulus, as compared to, for example, the Co—Cr alloy. Additionally, flow diversion stents composed of a percentage of tungsten (W) that is equal or larger than 10% of the platinum-tungsten (Pt—W) alloy have substantially low magnetic susceptibility for MR artifact, allowing MR follow up imaging for implanted flow diversion stents.

These one or more improved properties of the medical device composed of a percentage of tungsten (W) that is equal or larger than 10% of the platinum-tungsten (Pt—W) alloy may be achieved without having to increase the volume and/or weight of the device. Further, these improved properties are likely to be obtained when the volume and/or weight of the medical device is reduced as compared to devices that are at least partially formed from known materials, such as stainless steel, cobalt-chromium (Co—Cr), or platinum-tungsten (Pt—W) alloy having equal or less than 8% of tungsten (W).

Moreover, as long as the percentage of tungsten (W) is equal or larger than 10% of the platinum-tungsten (Pt—W) alloy, it should be appreciated that the percentage of platinum (Pt) in the alloy may be less than the 90% to 80% range, such that other materials may be present. In those embodiments, the platinum-tungsten (Pt—W) alloy may comprise smaller percentage (e.g., 5% or less) of other elements. For example, titanium (Ti) in order to obtain a reduced level of radiopacity, or zirconium (Zr), hafnium (Hf), and/or gold (Au) to achieve desirable levels of magnetic susceptibility, or tantalum (Ta), iridium (Ir), rhenium (Re), rhodium (Rh), ruthenium (Ru) and/or molybdenum (Mo) to obtain desirable levels of mechanical properties, including any combination thereof of these elements or any other suitable element.

Further, medical devices composed with the disclosed platinum-tungsten (Pt—W) alloy having a percentage of tungsten (W) that is equal or larger than 10% of the alloy, may include one or more materials that impart desired properties to the device so as to withstand the manufacturing processes that are needed to produce the device. These manufacturing processes include, for example, laser cutting, etching, crimping, annealing, drawing, pilgering, electroplating, electro-polishing, chemical polishing, cleaning, pickling, ion beam deposition or implantation, sputter coating, vacuum deposition, or the like.

By way of non-limiting examples, the disclosed platinum-tungsten (Pt—W) alloy is at least 95% of the medical devices. Further, the disclosed platinum-tungsten (Pt—W) alloy having a percentage of tungsten (W) that is equal or larger than 10% may be used to form devices such as for example: stents (e.g., slotted tube stents and/or braided or woven stents), filters, thromboembolic capture devices, flow diverters, vaso-occlusive devices, intrasaccular aneurysm implants, vascular delivery assemblies, catheters, reinforcement members, guidewires, delivery wires, radiopaque markers and the like.

By way of non-limiting examples, the disclosed platinum-tungsten (Pt—W) alloy having a percentage of tungsten (W) that is equal or larger than 10% of the alloy may be configured to at least partially form the medical device. For example, the alloy may form the majority weight percent of the medical device but that may not be required.

By way of example, the embodiment of FIG. 1A-3F depict implantable medical devices constructed with the disclosed platinum-tungsten (Pt—W) alloy having a percentage of tungsten (W) that is equal or larger than 10% of the alloy.

FIGS. 1A-1C illustrate an exemplary braided embolic device in the form of a tubular braided stent and/or flow diverter 10, constructed according to some embodiments. FIG. 1A shows the braided stent 10 in a radially expanded delivered configuration, having a proximal portion 12, a distal portion 14 and a lumen 16 extending therebetween. The braided stent 10 is formed out of a plurality of elongate members 20 (e.g., wires, drawn-filled tubes, threads, filaments and the like) that are woven together. FIG. 1B is a two-dimensional plan view of a section of a wall 18 of the braided stent 10, showing that the elongate braid members 20 are woven in a standard repeating "one-over, one-under" pattern 50 (detailed of FIG. 1A), which is a common weave pattern used in known braided embolic devices. One or more of the elongate members 20 are composed of the disclosed platinum-tungsten (Pt—W) alloy having a percentage of tungsten (W) that is equal or larger than 10%. The elongate members 20 of FIGS. 1A-1B can include a ribbon-like configuration having substantially rectangular cross-section (FIG. 1C). As further shown in FIG. 1C, the ribbon-like elongate members 20 comprise a width (W1) of 0.004 inch (0.102 mm) and a height (H1) of 0.002 inch (0.051 mm). In some embodiments, the ribbon-like elongate members 20 comprises a maximum width of 0.005 inch (0.127 mm) and a minimum height (thickness) of 0.0008 inch (0.0203 mm). In other embodiments, the ribbon-like elongate member 20 may have a maximum width of 0.002 inch (0.051 mm) and a minimum height of 0.0001 inch (0.00254 mm). In further embodiments, the ribbon-like elongate member 20 may have a cross-sectional dimension (width or thickness) that is less than 0.00085 inch. In further embodiments where the elongate members 20 have substantially circular cross-section (not-shown), the diameter of the circular cross-section of the elongate members 20 are in the range between 0.0008 inch (0.0203 mm) to 0.004 inch (0.102 mm), and preferably, in the range between 0.001 inch (0.025 mm) to 0.002 inch (0.051 mm). In other embodiments, the diameter of the circular cross-section of the elongate member 20 may be less than 0.00085 inch, and preferably between 0.0001 inch to 0.0008 inch, and more preferably between 0.0003 inch to 0.00075 inch. It should be appreciated that the elongate members 20 may include other cross-sectional configurations. For example, in other embodiments, the elongate member 20 may be a braid wire with a diameter that is anywhere from 0.0001 inch (0.00254 mm) to 0.0015 inch (0.0381 mm), and preferably anywhere from 0.0005 inch (0.0127 mm) to 0.001 inch (0.0254 mm).

In the embodiments of FIGS. 1A-1B, the braid pattern 50 or specification of the braid of the stent 10 includes between 24 to 144 elongate members 20; preferably between 48 to 120 elongate members 20, or between 24-72 elongate members 20. Additionally, the radially expanded delivered configuration of the braided stent 10 have a PPI between 30 to 200; preferably between 50 to 150.

Referring back to the disclosed platinum-tungsten (Pt—W) alloy having a percentage of tungsten (W) that is equal or larger than 10% forming one or more of the elongate members 20, provides the stent 10 with the following properties: a) the stent 10 would achieve higher radial force due to higher material modulus and strength; b) the stent 10 is configured to be manufactured of smaller elongate members 20 and with a greater wire count to achieve better flow diversion effect; c) the stent 10 is configured to have a reduced MR image artifact for follow up imaging procedures due to low magnetic susceptibility, making the stent 10 more suitable for MR imaging and/or the stent 10 is configured to have full radiopacity, and other advantages, previously disclosed. Further, if the radiopacity of the stent 10 is too high for the application, the device can be manufactured using a combination of elongate members 20 composed of the disclosed platinum-tungsten (Pt—W) alloy and another material or alloy with lower radiopacity, or the device can be manufactured using a composite wire that comprises the disclosed platinum-tungsten (Pt—W) alloy as an external layer and another less radiopaque alloy as the core. The above disclosed properties of the stent 10 composed of the disclosed platinum-tungsten (Pt—W) alloy having a percentage of tungsten (W) that is equal or larger than 10% forming one or more of the elongate members 20, are in comparison with stents composed of cobalt-chromium (Co—Cr) alloys or with stents made out of other available materials.

In other embodiments, the braided stent 10 may be made from an alloy containing rhenium. For example, the braided stent 10 may be made from a material containing molybdenum-rhenium (Mo—Re) alloy or tungsten-rhenium (W—Re) alloy. Also, in some embodiments, the material may further be alloyed with Ta, Ir, Rh, Ru, or any combination of the foregoing, to enhance mechanical property of the material. In further embodiments, the material may be further alloyed with Zr, Hf, Au, or any combination of the foregoing, to reduce magnetic susceptibility.

Figure 2B:
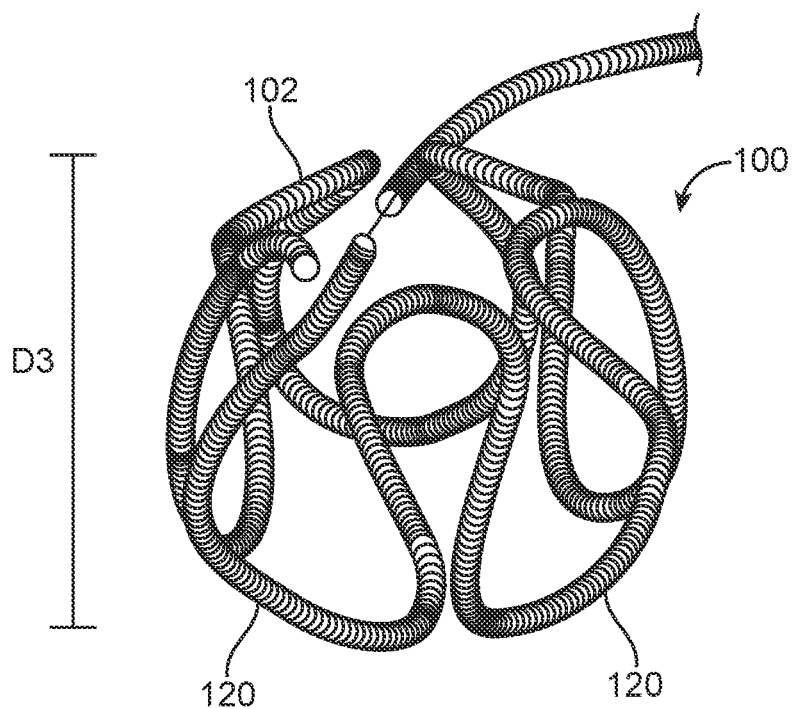

FIGS. 2A-2B illustrate an exemplary intrasaccular device in the form of an embolic coil 100, constructed according to some embodiments. The embolic coil 100 is another example of an implantable medical device. The coil 100 is formed of a helically wound wire 102 having a first end 104 and a second end 106. The coil 100 includes a stretch-resisting member 108 that is fixedly attached both to the first end 104 and to the second end 106. In alternative embodiments, the stretch-resisting member 108 may be attached to one of the two ends or to neither of the two ends. The coil 100 of FIG. 2A is shown in a "primary" winding or shape, and the coil 100 of FIG. 2B is shown in a "secondary" winding or shape. The secondary shape of the coil 100 of FIG. 2B forms a substantially spherical three-dimensional shape having non-overlapping loops 120. It should be appreciated that secondary shape of the coil 100 may assume any other suitable shape. The wire 102 of coil 100 may be formed of a single wire, drawn-filled tubes, threads, filaments or the like. In some embodiments, the wire 102 diameter (D1) ranges from about 0.0005 inch (0.0127 mm) to about 0.005 inch (0.127 mm), the primary wind diameter (D2) of the coil 100 ranges from about 0.003 inch (0.0762 mm) to about 0.030" (0.762 mm) and/or the secondary wind diameter (D3) ranges from about 0.5 mm to about 50 mm, as shown in FIGS. 2A-2B.

The wire 102 of coil 100 (FIGS. 2A-2B) is composed of the disclosed platinum-tungsten (Pt—W) alloy having a percentage of tungsten (W) that is equal or larger than 10%. Where the coil 100 is composed with the disclosed platinum-tungsten (Pt—W) alloy—as, for example compared to coils composed of platinum with 8% tungsten (Pt-8W)—the coil 100 includes the following properties: a) due to the higher modulus resulting in higher column strength the coil 100 is configured to support a longer length without corresponding larger wire 102; b) due to higher yield strength, the coil 100 is configured to be a more effective framing device; c) due to the stability of the alloy, the coil is configured to achieve better shape retention, and deliverability for coils to treat small aneurysms (e.g., under 2 mm due to combination of higher strength and higher modulus).

As previously disclosed, the coil 100 composed of the disclosed platinum-tungsten (Pt—W) alloy having a percentage of tungsten (W) that is equal or larger than 10% of the wire, has lower MR artifact due to low magnetic susceptibility as compared to the current coils composed of Pt-8% W alloy.

In other embodiments, the coil 100 may be made from an alloy containing rhenium. For example, the coil 100 may be made from a material containing molybdenum-rhenium (Mo—Re) alloy or tungsten-rhenium (W—Re) alloy. Also, in some embodiments, the material may further be alloyed with Ta, Ir, Rh, Ru, or any combination of the foregoing, to enhance mechanical property of the material. In further embodiments, the material may be further alloyed with Zr, Hf, Au, or any combination of the foregoing, to reduce magnetic susceptibility.

Figure 3A:
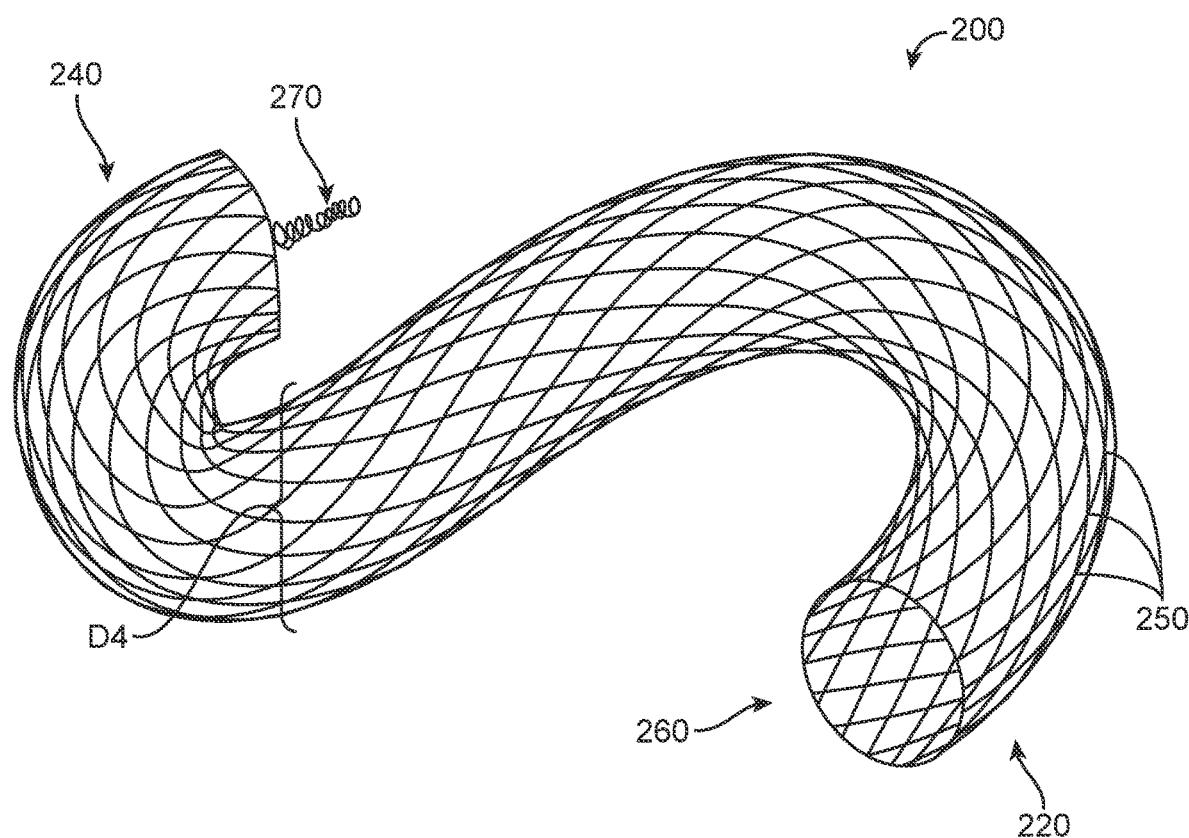
FIGS. 3A-3F are perspective views of an intravascular device constructed according to some embodiments.

FIGS. 3A-3F illustrate an exemplary braided intravascular device 200 having an atraumatic end member 270, constructed according to some embodiments. The braided intravascular device 200 is another example of an implantable medical device. FIG. 3A shows the braided intravascular device 200 in a radially expanded (i.e., unconstrained) configuration, having a proximal portion 220, a distal portion 240, and a lumen 260 extending therebetween. The braided intravascular device 200 is formed out of a plurality of elongate members 250 (e.g., wires, drawn-filled tubes, threads, filaments and the like) that are woven (or "braided") together. The braided intravascular device 200 includes the atraumatic member 270 (e.g., coil or the like) at the distal portion 240 of the device 200, as shown in FIG. 3A. It should be appreciated that another atraumatic member 230 may be disposed at the proximal portion 220 of the device 200 (shown in FIG. 3B). The individual elongate members 250 may have substantially circular cross-sections (FIG. 3C), with a cross-sectional diameter in a range of between about 0.0005 inch (0.0127 mm) to about 0.003 inch (0.0762 mm). The diameter (D4) of the intravascular device 200 may be in the range of between about 0.01 inch (0.25 mm) to about 0.2 inch (5 mm). It should be appreciated that the individual elongate members 250 may have other suitable cross-sections, such as for example, rectangular with rounded corners (FIG. 3D), rectangular with square corners (FIG. 3E), ovoid (FIG. 3F) or the like. The device 200 may also have different, i.e., non-tubular, cross-sectional shapes in their expanded configurations, such as a flattened rectangle with rounded corners (not shown).

Figure 3B:
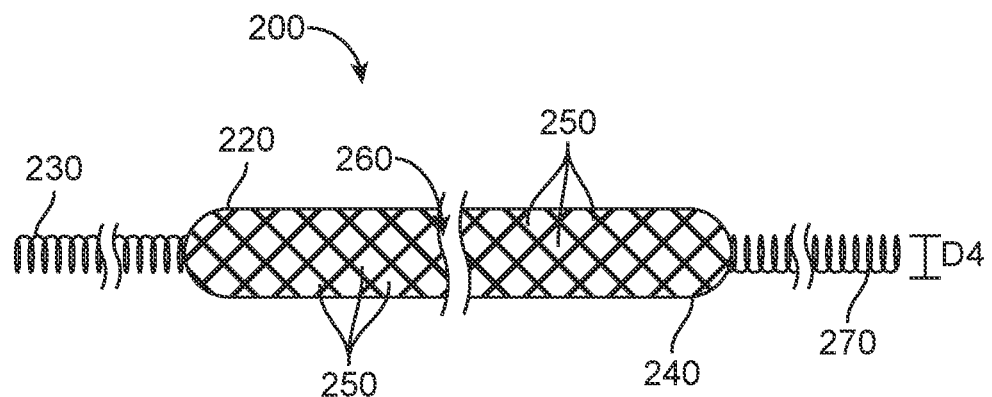
Figure 3C:
Figure 3D:
Figure 3E:
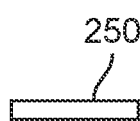
Figure 3F:

It should be noted that the braided intravascular device 200 of FIGS. 3A-3B is not limited to having the examples of the dimensions described, and that the braided intravascular device 200 may have other dimensions. For example, in some embodiments, the braided intravascular device 200 may comprise a braided structure formed from braid wires, wherein at least one of the braid wire may have a cross-sectional dimension that is anywhere from 0.0001 inch (0.00254 mm) to 0.001 inch (0.0254 mm). In other embodiments, the braid wire may have a cross-sectional dimension that is less than 0.00085 inch (0.022 mm), and preferably anywhere from 0.0001 inch (0.00254 mm) to 0.0008 inch (0.020 mm), and more preferably anywhere from 0.0003 inch (0.0076 mm) to 0.00075 inch (0.019 mm). Alternatively, the braided structure may be formed from ribbon wires, wherein at least one of the ribbon wires has a thickness that is at least 0.0001 inch (0.00254 mm), and a width that is at most 0.002 inch (0.0508 mm). In other embodiments, the ribbon wire may have a cross-sectional dimension (width or thickness) that is less than 0.00085 inch (0.022 mm), and preferably anywhere from 0.0001 inch (0.00254 mm) to 0.0008 inch (0.020 mm), and more preferably anywhere from 0.0003 inch (0.0076 mm) to 0.00075 inch (0.019 mm). Also, in other embodiments, the braided structure may be formed from one or more twisted wire. In addition, in some embodiments, the braided structure may have a wire count that is anywhere from 8 to 96, anywhere from 16-32, anywhere from 24-144, or anywhere from 24-72. Furthermore, in some embodiments, the braided structure may have a braid angle that is anywhere from 20° to 130°, or preferably anywhere from 20° to 60°, when the braided intravascular device 200 is unconstrained outside a delivery catheter.

Also, in some embodiments, the braided structure of the braided intravascular device 200 may have a tubular configuration. In other embodiments, the braided structure of the braided intravascular device 200 may have a non-tubular configuration. For example, in some embodiments, the braided structure may be a flat braid. A flat braid may be any braided structure with a cross-section having a width W and a thickness T (measured in a direction perpendicular to the width), wherein a ratio of W/T is equal to or greater than 2, 3, 4, 5, 6, 7, 8, 9, 10, 11, 12, 13, 14, 15, 16, 17, 18, 19, 20. Also, in some embodiments, the braided structure may be a ribbon braid. In one or more embodiments described herein, a braid may have a width that is anywhere from 0.020 inch (0.5 mm) to 0.197 inch (5 mm), and preferably anywhere from 0.030 inch (0.75 mm) to 0.079 inch (2.0 mm), and preferably anywhere from 0.030 inch (0.75 mm) to 0.06 inch (1.5 mm). In further embodiments, the braid may have a width that is 0.039 inch (1 mm) or larger. For example, in one implementation, the braid may have a width of about 1.25 mm (e.g., 1.25 mm+/−0.1 mm). In some embodiments, the braid may have a braid stiffness that is less than 50 mN/mm. Furthermore, in some embodiments, the braid may be formed from multiple braid wires of the same size and/or same composition. In other embodiments, the braid may be formed from multiple braid wires of different sizes and/or different compositions.

In some embodiments, when the braid is unconfined outside a catheter, the braid may have a first width, and when the braid is inside the catheter, it may elastically collapse and/or bend transversely (e.g., in a direction that is perpendicular to a longitudinal axis of the braid) to have a second width that is smaller than the first width. For example, the braid may be a flat braid that is curled or rolled up elastically to have the second width when inside the catheter, and may elastically spring into a relaxed configuration having the first width when deployed outside the catheter.

As shown in FIG. 3B, the atraumatic member 270 at the distal portion 240 of the braided intravascular device 200 is a first coil segment made from a coil wire. Optionally, the braided intravascular device 200 may also include another atraumatic member 230 at the proximal portion 220. The atraumatic member 230 is a second coil segment in the illustrated embodiments. In some embodiments, the coil segment (forming the atraumatic member 230/270) may comprise a coil wire having a cross-sectional dimension that is anywhere from 0.0001 inch (0.00254 mm) to 0.003 inch (0.075 mm), and wherein the first coil segment has a primary wind diameter that is anywhere from 0.003 inch (0.076 mm) to 0.030 inch (0.762 mm). In other embodiments, the braided intravascular device 200 may not include the atraumatic member 230 and/or the atraumatic member 270. The coil forming the atraumatic member 230/270 may have a simple or complex shape.

One or more of the elongate members 250 and/or the atraumatic member 230/270 are composed of the disclosed platinum-tungsten (Pt—W) alloy having a percentage of tungsten (W) that is equal or larger than 10% (such as 10%-20%, 10%-25%, or larger than 25%). Where one or more of the elongate members 250 and/or the atraumatic member 230/270 are composed with the disclosed platinum-tungsten (Pt—W) alloy, they include the following properties: a) due to the higher modulus resulting in higher column strength the intravascular device 200 includes a better transition between the elongate members 250 and/or the atraumatic member 230/270; b) the intravascular device 200 may comprise a smaller profile for delivery through smaller internal diameter catheters into a target site of a patient.

In other embodiments, the elongate members 250 may be made from an alloy containing rhenium. For example, the elongate members 250 may be made from a material containing molybdenum-rhenium (Mo—Re) alloy or tungsten-rhenium (W—Re) alloy. Also, in some embodiments, the material may further be alloyed with Ta, Ir, Rh, Ru, or any combination of the foregoing, to enhance mechanical property of the material. In further embodiments, the material may be further alloyed with Zr, Hf, Au, or any combination of the foregoing, to reduce magnetic susceptibility.

In some embodiments, the braided intravascular device 200 may be delivered through a catheter having a lumen for accommodating the braided intravascular device 200. The lumen of the catheter may have an internal diameter that is less than 0.020", less than 0.018", less than 0.016", or less than 0.014" (such as 0.013" or smaller). In other embodiments, the lumen of the catheter may have an internal diameter that is larger than 0.020", such as 0.04", 0.06", 0.08", 0.1", 0.2", etc.

In one or more embodiments described herein, the material forming the elongate member 20/102/250 may have a Young's modulus that is 30 Msi or higher, 36 Msi or higher, or 40 Msi or higher.

Also, in one or more embodiments described herein, the material forming the elongate member 20/102/250 may have an ultimate tensile strength (UTS) that is 350 ksi or higher, or 400 ksi or higher, or 470 ksi or higher, or 500 ksi or higher, such as anywhere from 500-700 ksi.

In accordance with some embodiments, experiments were conducted on devices composed of disclosed platinum-tungsten (Pt—W) alloy having a percentage of tungsten (W) that is equal or larger than 10% of the device or portions thereof. A sample wire made of the disclosed platinum-tungsten (Pt—W) alloy (Pt-16% W) and having a diameter of 0.0011" (0.02794 mm) was tested to confirm properties of the disclosed alloy and compared to the commonly used Pt-8% W with same wire diameter of 0.0011". Both wires having an elongation of approximately 2%. The sample wire composed of the disclosed platinum-tungsten (Pt—W) alloy (Pt-16% W) and having a density of 21.08 g/cm3 comprises an ultimate tensile strength (UTS) of 470 Ksi, a Young's modulus of 36 Msi and magnetic susceptibility of 23 ppm. In comparison, the commonly used Pt-8% W wire having a density of 21.26 g/cm3 has an ultimate tensile strength (UTS) of 200-250 Ksi, a Young's modulus of 26 Msi and magnetic susceptibility of 69 ppm.

Therefore, the wire composed of a platinum-tungsten alloy that is approximately 16% tungsten by weight showed approximately a 100% improvement in mechanical strength, approximately a 40% increase in Young's modulus, and approximately a 65% reduction in magnetic susceptibility, respectively, over a substantially identically dimensioned wire composed of a platinum-tungsten alloy that is approximately 8% tungsten by weight. Notably, in some embodiments, the implantable medical devices may be formed out of wires or filaments having the same attributes as the tested wire made from the platinum-tungsten alloy that is approximately 16% tungsten by weight.

In other embodiments where the elongate member 20/102/250 is formed from an alloy containing rhenium, similar mechanical properties may be obtained. For example, the rhenium-containing alloy may have a Young's modulus of 40 Msi or higher. The rhenium-containing alloy may have a UTS that is 400 ksi or higher, such as anywhere from 500 ksi to 700 ksi.

Figure 4:
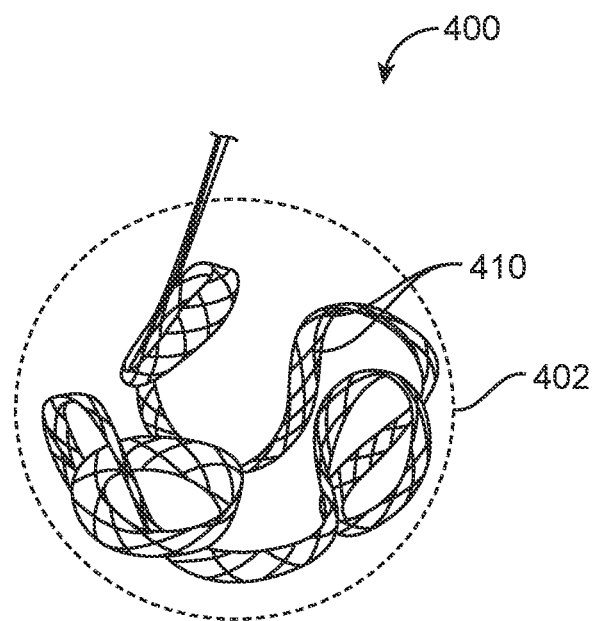
FIG. 4 illustrates an example of an implantable medical device in accordance with some embodiments.

FIG. 4 illustrates an example of an implantable medical device 400 in accordance with some embodiments. The implantable medical device 400 comprises a braided structure 402 made from a plurality of elongate members 410. Each of the elongate members 410 is a wire made from Pt—W alloy having a percentage of tungsten that is about 16% (e.g., 16%+/−2%) by weight. Also, each of the elongate members 410 has a cross-sectional dimension that is about 0.00075 inch (e.g., 0.00075 inch+/−0.0001 inch). The material of the elongate members 410 has a Young's modulus of 36 Msi, and ultimate tensile strength of 470 ksi. The braided structure 402 is a ribbon braid having a width of about 1.25 mm (e.g., 1.25 mm+/−0.1 mm).

Figure 5:
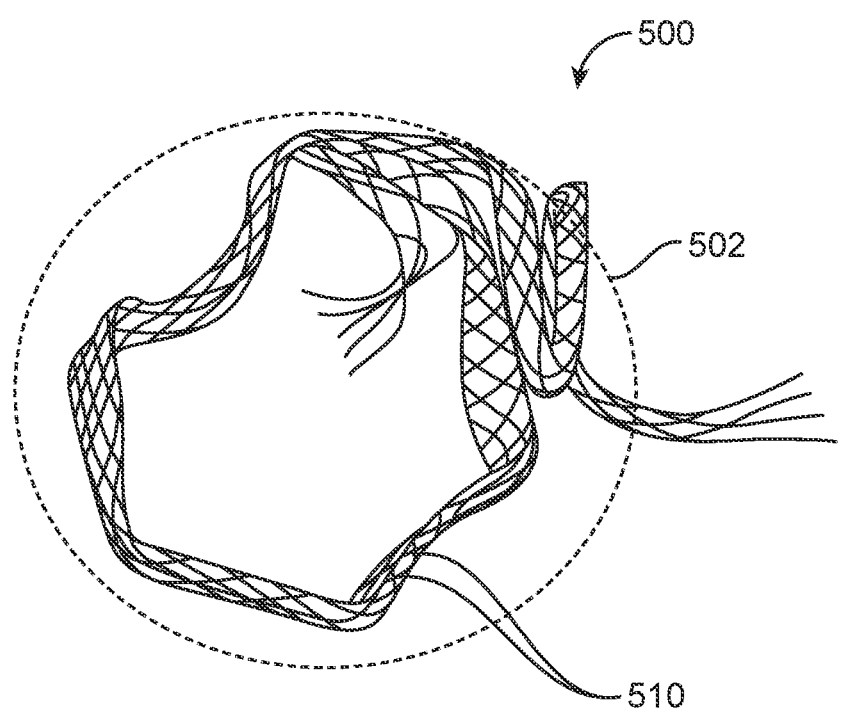
FIG. 5 illustrates another example of an implantable medical device.

The implantable medical device 400 has acceptable shape retention property, and can be delivered more smoothly using a catheter (e.g., a catheter with a lumen diameter of 0.013 inch), in comparison with another implantable medical device 500 shown in FIG. 5. The implantable medical device 500 of FIG. 5 is made from elongate members 510 having similar dimension as that of the elongate members 410, and is made by the same process as that for the implantable medical device 400. However, the elongate members 510 of the implantable medical device 500 are made from Pt—W alloy having a percentage of tungsten that is 8% by weight. In comparison to the shape retention of the implantable medical device 400 of FIG. 4, the loops of the implantable medical device 500 are easily unfolded, easily unbent, or easily plastically deformed (due to the lower material Young's modulus, which is 26 Msi), and therefore the implantable medical device 500 has undesirable shape retention property. Also, the Pt-8W material of the implantable medical device 500 has lower mechanical strength than Pt-16W, resulting in braids constructed of small diameter wires being easily damaged and/or easily disrupted during handling and/or processing. Sometimes, the wires forming the braid of the implantable medical device 500 may be broken due to the lower material UTS (250 ksi).

As shown in the above embodiments, using elongate members made from the materials described herein to make implantable medical devices are advantageous. This is because the higher Young's modulus (e.g., higher compared to Pt-8W) of the materials allow implantable medical devices with higher axial (column) stiffness and strength to be made. As a result, the implantable medical devices maybe even smaller in size (e.g., cross-sectional dimension) compared to previously known devices. In one application, the implantable medical device may be a vaso-occlusive device configured to be delivered to a small blood vessel to occlude an aneurysm. The small blood vessel may be any blood vessel in the body, including a distant blood vessel in a brain of a patient. Also, due to the higher mechanical strengths of the materials described herein, the implantable medical devices can be delivered smoothly using a small catheter without folding, buckling, and kinking. This is the case even if the medical device is made smaller in sized. In addition, due to the higher UTS of the materials, the elongate members forming the implantable medical devices will not easily be disrupted or break during handling and processing. Furthermore, because of the higher Young's modulus of the materials, smaller elongate members may be utilized to make implantable medical devices in order to achieve a softer bending stiffness. As a result, the implantable medical devices have desirable bending stiffness and can exhibit better shape retention properties.

In some embodiments, the implantable medical device described herein may be provided with a catheter. In such cases, the implantable medical device and the catheter together form a kit. The catheter may have a lumen with a cross-sectional dimension that is less than 0.02 inch (e.g., less than 0.014 inch). In some embodiments, the implantable medical device may be a flat braid that is accommodated in the lumen of the catheter. In such cases, the flat braid may have sufficient column strength to be advanced relative to the catheter (e.g., the flat braid will not buckle, kink, fold, etc., inside the lumen of the catheter as it is being advanced).

In some embodiments, the implantable medical device described herein may have a length that is anywhere from 1.2 inch (3 cm) to 19.7 inch (50 cm), and preferably from (2 inch) 5 cm to 11.8 inch (30 cm). Also, in one or more embodiments, the implantable medical device (e.g., a braid) with any of the length described herein is considered as having sufficient column strength if the implantable medical device, when inserted lengthwise into an elongate lumen, can be pushed through the elongate lumen without buckling, kinking, or plastically deformed, wherein the elongate lumen has a maximum lumen width of 0.02 inch, and preferably a maximum width of 0.016 inch, and even more preferably a maximum width of 0.014 inch (e.g., 0.013 inch). The elongate lumen may be a lumen of a catheter, or any elongate lumen, such as a lumen of a tube that is for use to test the column strength of the implantable medical device.

In some embodiments, the implantable medical device described herein is considered as having a sufficient shape retention property, if the implantable medical device with a certain initial radius R1 of curvature is inserted into a catheter, and has a radius R2 of curvature after the implantable medical device is deployed out of the catheter, wherein the radius R2 of curvature of the deployed implantable medical device is less than five times R1, or preferably less than four times R1, or more preferably less than 3 times R1, or even more preferably less than 2 times R1 (such as less than 1.5 times R1).

As used in this specification, the term "braid" refers to any structure formed by multiple elongate members, wherein the elongate members may or may not be woven to form the structure. In some embodiments, the braid may have a grid or mesh configuration with an open texture having spaced holes, wherein the spaced holes may form a certain uniform pattern, or may form a random pattern. In other embodiments, the braid may have other configurations, and may or may not have an open texture. In some embodiments, the elongate members may be coupled to each other by mechanical force, such as frictional force between the elongate members. By means of non-limiting examples, the frictional force coupling the elongate members to form the braid may be created by twisting the elongate members, weaving the elongate members, overlapping the elongate members, etc. In other embodiments, the elongate members may be coupled to each other by adhesive.

As used in this specification, the term "about" refers to a variation of a value that is within 10%, unless specifically stated otherwise. For example, equal to or greater than "about 10%" by weight refers to a weight that is at least 10%+/−1% of the total weight or higher.

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. An alloy comprising:
   platinum (Pt) and tungsten (W);
   wherein the platinum (Pt) and the tungsten (W) together constitute a majority of the alloy by weight;
   wherein a percentage of the tungsten (W) in the alloy is equal to or greater than 10% by weight and is less than 20% by weight;
   wherein the alloy further comprises zirconium (Zr), and a percentage of the (Zr) in the alloy is equal to or less than 5% by weight; and
   wherein the alloy has a Young's modulus that is 30 Msi or higher.

2. The alloy of claim 1, wherein the alloy has a magnetic susceptibility that is anywhere between 10 ppm to 300 ppm.

3. The alloy claim 1, wherein the alloy has a greater ultimate tensile strength, a greater Young's modulus, and a lesser magnetic susceptibility, than a platinum-tungsten alloy having a percentage of tungsten that is 8% by weight.

4. The alloy of claim 1, wherein alloy has an ultimate tensile strength that is greater than an ultimate tensile strength of a platinum-tungsten alloy having a percentage of tungsten that is 8% by weight.

5. The alloy of claim 1, wherein alloy has a Young's modulus that is greater than a Young's modulus of a platinum-tungsten alloy having a percentage of tungsten that is 8% by weight.

6. The alloy of claim 1, wherein the alloy has a magnetic susceptibility that is less than a magnetic susceptibility of a platinum-tungsten alloy having a percentage of tungsten that is 8% by weight.

7. A component of a medical device comprising the alloy of claim 1.

8. An implant comprising the alloy of claim 1.

9. A catheter comprising the alloy of claim 1.

10. A guidewire comprising the alloy of claim 1.

11. A delivery wire comprising the alloy of claim 1.

12. A marker comprising the alloy of claim 1.

13. An elongate member comprising the alloy of claim 1.

14. The elongate member of claim 13, wherein the elongate member is part of a braid.

15. The elongate member of claim 13, wherein the elongate member has a coil configuration.

16. The elongate member of claim 13, wherein the elongate member is a wire.

17. The elongate member of claim 16, wherein the wire has a diameter between 0.0005" to 0.005".

18. The alloy of claim 1, wherein a percentage of the platinum (Pt) and tungsten (W) is at least 95% by weight.

19. The alloy of claim 1, wherein the Young's modulus of the alloy is 36 Msi or higher.

* * * * *